United States Patent [19]

Matsuzawa et al.

[11] Patent Number: 5,403,716
[45] Date of Patent: Apr. 4, 1995

[54] METHOD FOR MEASUREMENT OF TISSUE FACTOR IN HIGH SENSITIVITY AND MEASUREMENT KIT THEREFOR

[75] Inventors: Kimihiko Matsuzawa, Hiroshima; Ryoichi Hasegawa, Iwakuni, both of Japan

[73] Assignee: Teijin Limited, Osaka, Japan
[21] Appl. No.: 924,030
[22] PCT Filed: Jan. 8, 1992
[86] PCT No.: PCT/JP92/00005
§ 371 Date: Sep. 3, 1992
§ 102(e) Date: Sep. 3, 1992
[87] PCT Pub. No.: WO92/12429
PCT Pub. Date: Jul. 23, 1992

[30] Foreign Application Priority Data

Jan. 10, 1991 [JP] Japan .................... 3-012478

[51] Int. Cl.$^6$ ............ G01N 33/544; G01N 33/551; G01N 33/577; G01N 33/535
[52] U.S. Cl. .................... 435/7.9; 435/7.92; 435/188; 435/810; 435/7.94; 436/518; 436/71; 436/524; 436/528; 436/826
[58] Field of Search .............. 435/7.4, 7.9, 7.92, 435/7.94, 13, 961, 962; 436/69, 825, 826, 531, 533; 530/388.25

[56] References Cited

U.S. PATENT DOCUMENTS

| 4,148,869 | 4/1979 | Deaton | 424/1 |
| 4,810,630 | 3/1989 | Craig et al. | 436/825 X |
| 5,017,559 | 5/1991 | Dosako et al. | 514/21 |

FOREIGN PATENT DOCUMENTS

| 48-37184 | 6/1973 | Japan . |
| 59-60260 | 6/1984 | Japan . |
| 60-4938 | 2/1985 | Japan . |
| 1-217266 | 8/1989 | Japan . |
| 1-503438 | 11/1989 | Japan . |
| 2-19766 | 1/1990 | Japan . |
| 2-203795 | 8/1990 | Japan . |
| 2-216054 | 8/1990 | Japan . |
| WO8807543 | 10/1988 | WIPO . |

OTHER PUBLICATIONS

Derwent Abstract for JP48-37184.
P1530 Abstract for Kubota et al, Thromb. Haemostas. 54, 258, 1985.
Nemberson, Y., J. Clin. Invest. 47, 72–80, 1968.
Bjorklid, E., et al., Br. J. Haematol. 39, 445–459, 1978.
Andoh, K. et al., Thromb. Res. 43, 275–287, 1986.
Derwent Abstract for JP59–60260.
Derwent Abstract for JP-19766.
Spicer, E. K. et al., Proc. Natl. Acad. Sci. USA 84, 5148–5152, 1987.
Morrissey, J. H. et al., Cell 50, 129–135, 1987.
Scarpati, E. M. et al., Biochemistry 26, 5234–5238, 1987.
Bach, R. et al., Biochemistry 25, 4007–4020, 1986.
Fair, D. S. et al., J. Bio. Chem. 262, 11692–11698, 1987.
Weiss, H. J. et al., Blood 73, 968–975, 1989.
Calbiochem Corporation A Guide to the Properties and Uses of Detergents in Biology and Biochemistry (1988) pp. 4–12.

Primary Examiner—Esther M. Kepplinger
Assistant Examiner—Nancy J. Parsons
Attorney, Agent, or Firm—Wenderoth, Lind & Ponack

[57] ABSTRACT

The present invention provides an improved buffer solution for conducting an immunological method for measuring apoprotein of human tissue factor, and a kit therefor. More specifically, in a method for immunologically measuring the presence or concentration of apoprotein of human tissue factor contained in a sample, which method includes the steps of (1) forming in a buffer solution a ternary complex of (a) a first monoclonal antibody which is capable of specifically binding to the apoprotein and is immobilized on a solid carrier insoluble in the buffer solution, (b) the apoprotein and (c) a labeled second monoclonal antibody which is capable of specifically binding to the apoprotein at a different site from the binding site of the first monoclonal antibody, and (2) measuring the amount of labeled second monoclonal antibody in the ternary complex to determine the presence or concentration of apoprotein in the sample, the improvement of this invention comprising employing a buffer solution (i) containing in a concentration of 2 to 15 weight % at least one nonionic surfactant having an HLB value within a range of 12 to 30, and
(ii) containing a protein having a molecular weight of about 16,000 to about 50,000 and an isoelectric point of 1.0 to 5.0.

24 Claims, 4 Drawing Sheets

* unmeasurable

SEQUENCE LISTING ( 1 ) GENERAL INFORMATION:

( i i i ) NUMBER OF SEQUENCES: 2

(2) INFORMATION FOR SEQ ID NO:1:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION: 1-24
        (C) IDENTIFICATION METHOD:
        (D) OTHER INFORMATION: /note ="26th to 49th amino acid
            residues of human tissue factor"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:1:

```
Glu  Pro  Lys  Pro  Val  Asn  Gln  Val  Tyr  Thr  Val  Gln  Ile  Ser  Thr  Lys
 1              5                        10                       15
Ser  Gly  Asp  Trp  Lys  Ser  Lys  Cys
             20
```

(2) INFORMATION FOR SEQ ID NO:2:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:

```
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-22
        ( C ) IDENTIFICATION METHOD:
        ( D ) OTHER INFORMATION: /note ="146th to 167th amino acid
                residues of human tissue factor"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

Val  Phe  Gly  Lys  Asp  Leu  Ile  Tyr  Thr  Leu  Tyr  Tyr  Trp  Lys  Ser  Ser
1                  5                      10                      15

Ser  Ser  Gly  Lys  Lys  Thr
                20
```

METHOD FOR MEASUREMENT OF TISSUE FACTOR IN HIGH SENSITIVITY AND MEASUREMENT KIT THEREFOR

BACKGROUND OF THE INVENTION

1. Field of the Invention

This invention relates to a method for measuring the tissue factor in a specimen in high sensitivity and a kit used for measurement thereof. More specifically, this invention relates to a method for immunologically measuring the human tissue factor in a human specimen in high sensitivity by a sandwich method, and a kit used for measurement thereof.

2. Description of Related Art

A tissue factor is a lipoprotein which is involved in the blood coagulation reaction and has hitherto been called "tissue thromboplastin" or "coagulation factor III", and it is a kind of conjugated protein comprising a lipid part and the protein part (apoprotein).

Because of its extremely low content in living bodies and difficulty in purification, research into of the tissue factor on a molecular level has been delayed, but the cDNA of the apoprotein of the human tissue factor was cloned and the base sequence and amino acid sequence thereof were determined, in succession, in 1987 by three research groups (Spicel, E. R., et al. : Proc. Natl. Acad. Sci. USA 84, 5148 (1987), Morrissey, J. H., et al. : Cell 84, 129 (1987), Scarpati, E. M., et al., : Biochemistry 26, 5234 (1987). They report that the apoprotein of the human tissue factor comprises 263 amino acid residues and its molecular weight by the SDS-electrophoresis method is 47 KD.

Tissue factors exist in almost all the biotissues of various animals including human beings, and particularly, are distributed, in comparatively large quantities, in the circulatory system, for example in the brain, lungs and placenta, throughout which blood vessels are provided, and vascular endothelia, and usually, are expressed and exist as a membrane protein on the membrane of the cells of these tissues.

Further, their physiological action is to bear the initiation reaction of a series of extrinsic coagulation reactions caused by damages and breakdown of blood vessels. Specifically, in the presence of $Ca^{++}$, they form a molecule complex with coagulation factor VII to activate both of coagulation factors X and IX, and as a result form fibrin gel in cooperation with intrinsic coagulation reaction. Namely, tissue factors as well as factor VII are proteins playing a central role in the initiation mechanism of extrinsic coagulation reaction. (Bach, R., et al. : Biochemistry 22, 4007 (1986), Fair, D. S., et al. : J. Boil. Chem. 262, 11692 (1987), Weiss, H. I., et al.,: Blood 73, 968 (1989)).

Tissue factors having the physiological actions described above have drawn attention as an important factor for blood coagulation. Thus, they play an extremely important role in researche in the basic medicine and clinical medicine of the circulatory system to measure easily and accurately a very small quantity of the human tissue factor in a specimen.

As methods to measure the human tissue factor in a specimen, several methods have hitherto been proposed. A representative example thereof is a method, called the method of Nemerson, to measure tissue factor activity by two stage steps (Nemerson, Y., J. Clin. Invest. 47 72 (1968). To put it briefly, the measurement method is one to judge tissue factor activity by adding to a specimen a mixed solution of coagulation factors VII and X to carry out reaction for a certain time, and then adding this reaction solution to normal plasma to which a crude phospholipid is added and measuring coagulation time. However, this method has a problem that since the stability of the reagents used is low and it is difficult to measure coagulation time with good accuracy, it is difficult to measure easily a very small quantity of the human tissue factor in a solution. Further, the above method is an indirect measurement method wherein tissue factor activity is judged by measuring coagulation factor Xa, and therefore, as a matter of course, there is a limit to its accuracy. Other tissue factor measurement methods proposed based on activity measurement have each the above problems.

On the other hand, the following are reported as immunological measurement methods for tissue factors. One is radioimmunoassay (abbreviated as RIA) by Bjorklid, E., et al. (Bjorklid, E., et al. Br. J. Haematol. 39, 445 (1978)). Another is RIA by Andoh, K., et al. (Andoh, K., et al., Thromb. Res. 43, 275 (1986), Kubota, T., et al., Thromb. Haemostas. 54, 258 (1985)). Both methods are competition methods using polyclonal antibodies alone, and had a problem in specificity for the human tissue factor. Further, both methods take very long measurement time, and that is, the former takes 36 hours and the latter 51 hours. Therefore, both methods have only low practicability in view of accuracy, easiness of measurement, etc.

Thereafter, measurement methods using monoclonal antibodies were disclosed in (i) Japanese Tokuhyohei No. 503438/1989, (ii) Japanese Laid-Open Patent Publication No. 203795/1990 and (iii) Japanese Laid-Open Patent Publication No. 216054/1990. According to the researche by the present inventors, it was found that since the human tissue factor in a specimen usually forms an apoprotein-lipid complex, an immune reaction with the apoprotein is hindered, and its content in normal human blood, e.g. serum or plasma is very small and on the patents in order of Pg (pico-gram)/ml. When the methods of the (i) to (iii) above are checked from such viewpoints, specifically in the above patent (i), although in detection of the human tissue factor in a sample from a body by a sandwich method, use of TBS/TRITON (Tris buffered saline/TRITON) is disclosed as an immune reaction solution, there is no disclosure about measurement of the tissue factor in a human specimen, especially measurement of the tissue factor in human blood, e.g. serum or plasma.

As for the methods of the patents in the above (ii) and (iii), although it is disclosed to use as an immune reaction solution an aqueous solution containing a buffer solution having a pH of around neutrality such as a phosphate, Tris or Hepes buffer and a nonpolar solubilizer such as TRITON or TWEEN, there is no disclosure about measurement of the tissue factor in human blood, e.g. serum or plasma, as is the case with the method of the of the above (i).

SUMMARY OF THE INVENTION

Thus, the first object of this invention lies in providing a method for immunologically measuring the human tissue factor in a specimen in high sensitivity by a sandwich method, and a kit therefor.

The second object of this invention lies in providing a method for immunologically measuring accurately and in high sensitivity the tissue factor contained in a very small quantity in human blood, particularly serum or plasma as a specimen, and a kit therefor.

Another object of this invention lies in providing a method for immunologically measuring in a short time and by an easy operation the tissue factor contained in a very small quantity in a human specimen, particularly human blood, and a kit therefor.

According to the researche by the present inventors, the objects and advantages of the above present invention were found to be accomplished by, in methods for immunologically measuring the tissue factor in a specimen in a buffer solution by immune reaction, a method for measuring the tissue factor in high sensitivity which comprises (a) using a monoclonal antibody (first antibody) specifically recognizing the apoprotein of the human tissue factor and immobilized on an insoluble carrier, and a labeled monoclonal antibody (second antibody) specifically recognizing the apoprotein of the human tissue factor and having a recognition site different from that by the first antibody, and (b) carrying out the immune reaction in a buffer solution
  (i) containing in a concentration of 2 to 15 weight % at least one nonionic surfactant having an HLB (hydrophilic-lipophilic balance) value of 12 or more, and
  (ii) containing a protein having a molecular weight of about 16,000 to about 50,000 and an isoelectric point of 1.0 to 5.0, or a mixture containing the protein.

Further, according to the researche of the present inventors, the above measurement method is found to be accomplished by use of, in kits for immunologically measuring the tissue factor in a specimen wherein are combined (a) a first antibody,
(b) a second antibody (labeled antibody),
(c) a buffer solution,
(d) a washing solution and
(e) in case of use of an enzyme-labeled antibody as the second antibody, a substrate for measuring enzyme activity and a reaction-stopping agent, a kit for measuring the tissue factor in the specimen in high sensitivity wherein (1) the first antibody of (a) is a monoclonal antibody specifically recognizing the apoprotein of the human tissue factor and immobilized on an insoluble carrier, and the second antibody of (b) is a labeled monoclonal antibody specifically recognizing the apoprotein of the human tissue factor and having a recognition site different from that by the first antibody, and (2) as themselves or in solution state(s) thereof are further combined
  (i) at least one nonionic surfactant having an HLB (Hydrophilic-lipophilic balance) value of 12 or more, and
  (ii) a protein having a molecular weight of about 16,000 to about 50,000 and an isoelectric point of 1.0 to 5.0, or a mixture containing the protein.

Hereafter, the measurement method and kit therefor of this invention are described in more detail.

(A) Monoclonal antibodies and preparation thereof:

In the measurement method and kit therefor of this invention, two kinds of monoclonal antibodies are used, and each monoclonal antibody specifically recognizes the apoprotein of the human tissue factor.

A human tissue factor apoprotein as an antigen to obtain such monoclonal antibodies may either be one of a natural type extracted from a natural material or one having immunological properties analogous to the natural type of human tissue factor apoprotein and obtained by a protein engineering method or a gene engineering method. An example thereof may be a hapten, namely a peptide containing the antigen determination site of the natural type of human tissue factor apoprotein. Further, it may be a fragment obtained by decomposing the human tissue factor apoprotein either with a proteolytic enzyme such as, for example, trypsin, chymotrypsin or pepsin or with a proteolytic reagent such as, for example, cyanogen bromide. As examples thereof, there can, for example, be mentioned a peptide at the N-terminal region, a peptide at the C-terminal region and a peptide at the intermediate region, etc. of the human tissue factor apoprotein.

As materials for obtaining the natural type of human tissue factor apoprotein, there can, for example, be mentioned human brains, human lungs, human placentas or the like. Separation and purification thereof can be carried out by combination of conventional membrane protein separation techniques such as, for example, extraction, salting out, centrifugation, ultrafiltration, various chromatographies, etc., and as example thereof, there can be mentioned the method disclosed in the above Japanese Tokuhyohei No. 503438/1989.

A monoclonal antibody can be prepared by culturing a hybridoma prepared by the cell fusin method by Koehler and Milstein (G. Koehler and C. Milstein, Nature (London) 256, 495 (1975)) using an antigen thus obtained, to secrete it, and separating it from the culture medium. Namely, a mouse is immunized with the human tissue factor apoprotein antigen, and lymphocytes of this mouse are fused with mouse myeloma cells, respectively, to produce hybridomas. The hybridomas thus obtained produce various monoclonal antibodies in accordance with the various lymphocytes fused, respectively, and therefore, a hybridoma producing a desired monoclonal antibody is isolated by cloning as a cloned hybridoma. This cloned hybridoma is cultured in vitro or in vivo and the monoclonal antibody is separated.

As preferred examples of such monoclonal antibodies, there can be mentioned monoclonal antibodies which do not lose their antibody activities in the presence of nonionic surfactants in this invention. Further, there can be mentioned a monoclonal antibody binding to an epitope at a position free of steric hindrance of the human tissue factor apoprotein. For example, there can be mentioned a monoclonal antibody capable of specifically recognizing the apoprotein of the human tissue factor and neutralizing the binding ability of the human tissue factor to coagulation factor VII/VIIa. As such monoclonal antibodies capable of neutralizing the binding ability of the human tissue factor to the coagulation factor VII/VIIa, there can, for example, preferably be mentioned monoclonal antibodies which do not react with any sites of the 204th to 226th amino acid residues of the amino acid sequence of the human tissue factor (the amino acid sequence of FIG. 1 disclosed in Japanese Tokuhyohei No. 503438/1989). Preferred among them are the combination of a monoclonal antibody immunely reacting with the human tissue factor heavy chain protein and the following polypeptide (I) consisting of the 26th to 49th amino acid residues of the amino acid sequence of the human tissue factor, with a monoclonal antibody immunely reacting with the human tissue factor heavy chain protein and the following polypeptide (II) consisting of the 146th to 167th amino acid resides of the amino acid sequence of the human tissue factor.

EPKPVNQVYTVQISTKSGDWKSKC    (I)(SEQ ID NO:1)

VFGKDLIYTLYYWKSSSSGKKT      (II)(SEQ ID NO:2)

The amino acid sequences of the above (I) and (II) are expressed by one letter symbols for amino acids.

A particularly preferred combination of monoclonal antibodies in this invention is the combination of the antibody (TF8-5G9) produced by hybridoma TF8-5G9 deposited with ATCC as an accession number of HB9382 as one of the monoclonal antibodies and the antibody (TF9-6B4) produced by hybridoma TF9-6B4 deposited with ATCC as an accession number of HB9381 as the other (These monoclonal antibodies are disclosed in the above Japanese Tokuhyohei No. 503438/1989).

(B) Immunoassay system:

It is possible to measure a very small quantity of the human tissue factor in high sensitivity, accurately and easily, using the aforesaid two kinds of monoclonal antibodies, by a sandwich method based on enzyme immunoassay (EIA), fluoroimmunoassay (FIA), chemiluminescene immunoassay (CLIA), RIA or the like in the method of this invention.

In the sandwich method of this invention, one of the above monoclonal antibodies is used as an antibody immobilized on an insoluble carrier (first antibody), or the other is used as a labeled antibody (second antibody). Further, as an antibody molecule to be used in this invention, any antibody molecule can be used so long as it holds a binding ability to the antigen, and examples thereof are a complete antibody (whole molecule), F(ab')$_2$, Fab' or Facb fragment, etc. F(ab')$_2$ or Fab' is preferred as such a fragment, and they can be obtained by subjecting a monoclonal antibody thus obtained to known method(s), for example by decomposing it with pepsin to give F(ab')$_2$ fragment, or further subjecting the F(ab')$_2$ fragment to reduction treatment to give Fab' fragment (Nisonoff, A., et al. : Arch. Biochem. Biophys. 89, 230 (1960), Parham, P: J. Immunol. 131, 2895 (1983), etc.).

An anti-human tissue factor apoprotein monoclonal antibody immobilized on an insoluble carrier (first antibody) can be obtained as follows.

As insoluble carriers, there can be mentioned (1) naturally occurred polymers and their derivatives, (2) synthetic polymers and their derivatives, and further (3) metal oxides and mixtures of metal oxides with the above polymers. Included in the first group are polysaccharides and their derivatives such as, for example, cellulose, SEPHADEX, SEPHAROSE, carboxymethylcellulose, nitrocellulose, cellulose acetate and dextran; inorganic polymers such as glass and silica gel; etc. Further, included in the second group are vinyl polymers such as, for example, polystyrene, polyethylene, polypropylene, ABS, (acrylonitrile-butadiene-stylene copolymer) polyvinyl fluoride, polyamine-methyl vinyl ether-maleic acid copolymers and ethylene-maleic acid copolymers; condensation polymers including polyamides such as, for example, 6-nylon, 6,6-nylon and amino acid polymers, polyesters such as polyethylene terephthalate; etc. Further, included in the third group are iron oxides such as triiron tetroxide, a mixture of triiron tetroxide with polystyrene; a carrier consisting of triiron tetroxide coated with polystyrene; etc. Further, their shapes or forms are not particularly limited and they may, for example, be in a shape or form of a test tube, microtiter plate, beads, latex particles, granulated particles, membrane or the like. Preferred among them are beads having a mirror-like surface.

As an antibody to be immobilized onto such an insoluble carrier, there can be mentioned the complete antibody (whole molecule) or a fragment such as F(ab')$_2$, Fab', Fab or Facb of the aforesaid anti human tissue factor apoprotein monoclonal antibody, or a derivative of the antibody molecule or a fragment thereof holding binding ability to the antigen. Preferred among them is the complete antibody or F(ab')$_2$ fragment.

As a method to immobilize such an antibody on the insoluble carrier, there can be used a physical adsorption method such as, for example, a method comprising immersing polystyrene beads in an antibody solution; an ionic bind method such as, for example, a method using an ion exchange resin or a carrier having an ionizing function group such as an amino group, a carboxylic acid group, a sulfuric acid group or a phosphoric acid group; a covalent bond method based on chemical reaction such as, for example, a carboxy-chloride method, a carbodiimide method, a maleic anhydride derivative method, an isocyanate derivative method, a cyanogen bromide-activated polysaccharide method, a diazo method, an active ester method or a carrier binding method using a crosslinking agent (as the crosslinking agent is used glutaraldehyde, hexamethylene isocyanate, succinimide, a maleimide compound or the like); further, a method to bind the antibody to the carrier, for example, via a substance which does not have binding ability to the human tissue factor but is capable of binding to the antibody by biological reaction, for example a method using a carrier bound to protein A; etc.

It is preferred to use as the insoluble carrier, particularly, an insoluble carrier consisting of a material having a mirror-like surface, because when such a carrier is used, nonspecific adsorption is only in a low level and measurement sensitivity increases. As such an insoluble carrier having a mirror-like surface, there can be mentioned one wherein the center line average roughness (Ra) of its surface is 1.5 μm or less. The center line average roughness can be measured by a surface roughness shape-measuring machine, for example Surfcom 570A (produced by Tokyo Seimitsu Co., Ltd.).

The center line average roughness (Ra) means a value obtained by expressing in a micron unit the value of Ra given by the following equation when a portion of a measurement length of l in the direction of the center line of the roughness curve is extracted from the roughness curve, and the center line of this extracted portion, the direction of longitudinal magnification and the roughness curve are expressed as X axis, Y axis and Y=f(x), respectively.

$$Ra = \frac{1}{l} \int_o^l /f(x)/d(x)$$

Description on this center line average roughness (Ra) is made in JIS B0601-1982 (Japan), ANSI B46.1-1979 (USA) and R468-1966 (ISO).

In the following examples of this invention, the surface roughness of insoluble carriers was measured using a surface roughness tester Surfcom® 570A produced by Tokyo Seimitsu Co., Ltd.

The material and shape of the above insoluble carrier having a smooth surface are not particularly limited, and those described above are mentioned. Particularly preferred example is polystyrene beads.

When an anti-human tissue factor apoprotein antibody immobilized on an insoluble carrier according to the invention thus obtained is used, it is possible to measure a very small quantity of the tissue factor accurately and easily.

Next, a labeled monoclonal antibody (labeled antibody) used as the second antibody in this invention can be obtained as follows.

As an antibody usable as the second antibody, there can be mentioned a complete antibody (whole molecule), its Fab', F(ab')$_2$ or Fab fragment, or the like, as described above. Preferred among them is the complete antibody, Fab' fragment or F(ab')$_2$ fragment. As a labeling substance, there can be mentioned a radioisotope such as $^{125}$I, a fluorescent substance such as fluorescein, a chemiluminescent substance such as an acridinium ester, further an enzyme, or the like, but preferably, an enzyme having an amplifying action is more suitable.

As an enzyme to be bound to the monoclonal antibody, there can be exemplified, for example, lysozyme, malate dehydrogenase, glucose-6-phosphate dehydrogenase, peroxidase, glucose oxidase, alkaline phosphatase, luciferase, $\beta$-galactosidase, alcohol dehydrogenase, invertase or the like.

Binding of such an enzyme to the monoclonal antibody can be carried out according to a usual method such as a glutaraldehyde method, a periodic acid method or a maleimide method. For example, such binding can be carried out by reacting a maleimidated antibody or fragment of an antibody with a thiolized enzyme in a solution. Maleimidation of the antibody or fragment of the antibody can, for example, be carried out using succinimdyl 4-(N-maleimidomethyl)cyclohexane carbonate (SMCC), succinimidylmethamaleimidobenzoate (MBS), succinimidyl-6-maleimidohexanoate (EMCS) or the like. Introduction of thiol group(s) into the enzyme can be carried out by a known method ["Koso Meneki Sokuteihou" (Enzyme Immunoassay) edited by Ishikawa, published by Igakushoin, 1978]. For example, such introduction can be carried out by reacting the enzyme with S-acetylmercaptosuccinic anhydride (AMSA), N-succinimidyl-3-(2-pyridylthio)propionate (SPDP) or the like.

In case an enzyme is used as a labeling substance in the measurement method of this invention, a substrate for measurement of the activity of the enzyme usually known in immunological measurement can be used in accordance with the kind of the enzyme.

As examples thereof, substrate of peroxidase include 2,2'-azino-di-[3-ethylbenzothiazolinesulfonic acid] diammonium salt (ABTS)-H$_2$O$_2$, orthophenylenediamine (OPD)-H$_2$O$_2$, 3,3',5 5'-tetramethylbenzidine (TMB)-H$_2$O$_2$, tyramine-H$_2$O$_2$, 3-(p-hydroxyphenyl)propionic acid-H$_2$O$_2$, luminol-H$_2$O$_2$, pyrogallol-H$_2$O$_2$, luciferin, etc., and substrates of alkaline phosphatase include 4-nitrophenyl phosphate, 4-methylumbelliferyl phosphate, NADP, phenolphthalein monophosphate, adamantyl-1,2-dioxetane allyl phosphate (AMPPD), etc.

Substrates of $\beta$-galactosidase include 2-nitrophenyl-$\beta$-D-galactoside, 4-methylumbelliferyl-$\beta$-D-galactoside, etc.

Substrates of luciferase include FMNH$_2$—R—CHO—O$_2$, etc.

It is possible to measure a very small quantity of a tissue factor accurately and easily, using the labeled antibody of this invention thus obtained.

In this invention, in a buffer solution where immune reaction is carried out are made to exist ① one or two or more of nonionic surfactants having an HLB (hydrophile-lipophile-balance) value of 12.0 or more, and ② a protein having a molecular weight of about 16,000 to about 50,000 and an isoelectric point of 1.0 to 5.0, or a mixture containing the protein; and the tissue factor in a specimen is measured. By making the surfactant and the protein or the like coexist, a new effect by using them together is exerted, without losing their respective intrinsic effects in the immune reaction solution. According to this invention, by cooperation of the surfactant effect, the protein effect and the effect by using them together, it becomes possible to measure the tissue factor in a specimen in high sensitivity, accurately, only in a small measurement error, in a short time and easily. This is detailedly described below.

The human tissue factor in a specimen usually forms an apoprotein-lipid complex, and thus immune reaction of the antibody with the apoprotein is hindered. As a result, there arises a striking difference in immune reactivity between the apoprotein as a standard substance for obtaining a calibration curve and the apoprotein in the specimen. Therefore, there arise inconveniences, for example that only inaccurate measured values are obtained or measurement time is elongated.

When only the above surfactant is made to exist (without using the protein) in the immune reaction solution, the problem that there arises a difference in immune reactivity between the standard substance apoprotein and the apoprotein in the specimen is solved by its surfactant effect, and it becomes possible to obtain accurate measured values and at the same time remarkably shorten measurement time. However, in this case, since nonspecific adsorption cannot sufficiently be inhibited, background is high and it is impossible to obtain a sensitivity to measure a very small quantity of the tissue factor.

On the other hand, when the protein or the mixture containing the protein is used solely without coexistence of the above surfactant, nonspecific adsorption in immune reaction is inhibited, and thus background lowers and high sensitivity is obtained. However, in this case, the above problem on measurement of the human tissue factor in the specimen is not solved, and thus it is impossible to make the measurement accurately and in a short time.

When both of the protein and the surfactant are made to coexist in the immune reaction solution based on this invention, the effects which both of them have are manifested at the same time, and it becomes possible to measure in a short time, in high sensitivity and accurately the apoprotein which exists in a very small quantity in a specimen and forms complexes with the lipids. More surprisingly, by making both of them coexist, an effect by using them together, not obtained only by one of them, is accomplished that the tissue factor in the specimen can be measured with a remarkably small measurement error.

The measurement error referred to herein does not mean a systematic error caused by individual habits, inaccuracy of a measurement instrument, badness of reagents or the like, but means "an error which occurs by causes incapable of being attributed and gives dispersion to measured values", namely an accidental error. Therefore, the magnitude of errors is expressed by standard deviation, a coefficient of variation (CV) or the like. A measurement method giving only a small measurement error is indispensable for obtaining accurate measured values in high sensitivity, and particularly requisite in development of an immunological measurement method wherein complicated factors are mutually involved. Since, in accidental errors, dispersion of measured values is considered to be the result of the total of many factors in all the measurement steps, the reason of manifestation of the effect by using them together is not clear, but is surmised as follows. Namely, it is known that the above surfactant generally has an action to denature proteins and at the same time has an action to inhibit immune reactions. On the other hand, the protein, for example skim milk is sparingly soluble in water at a concentration above 0.8% and forms suspensions, and thus is a protein comparatively slow to get compatible with water. Thus, the protein is not considered, in case of sole use, to dissolve completely in the immune reaction solution as an aqueous solution. However, when the surfactant is made to coexist, it is considered that the solubility of the protein (skim milk) is enhanced, not only the nonspecific adsorption inhibition effect of the protein (skim milk) but the effect thereof to inhibit the protein denaturation action and immune reaction inhibition action of the surfactant are manifested in the immune reaction solution, and therefore the stability of the immune reaction increases. The present inventors name such a substance having an effect to increase the stability of an immune reaction a "antigen-antibody reaction regulating agent." Namely, the protein acts as an antigen-antibody reaction regulating agent. It is surmised that as a result, measurement errors are remarkably improved in the measurement method of this invention.

As for surfactants to be used in this invention, any nonionic surfactants having an HLB value of 12.0 or more can be used so long as they do not highly inhibit the antigen-antibody reaction. Further, such nonionic surfactants can be used alone or in a combination of two or more. Preferred are nonionic surfactants having an HLB values of 12.5 to 30.0. Herein, the HLB value in case of use of a mixture of two nonionic surfactants can be calculated by the following equation.

(The HLB value of a mixture) = $V_A \times HLB_A + V_B \times HLB_B$

[$V_A$: the volume ratio of nonionic surfactant A,
$HLB_A$: the HLB value of nonionic surfactant A,
$V_B$: the volume ratio of nonionic surfactant B,
$HLB_B$: the HLB value of nonionic surfactant B]

The nonionic surfactants include, for example, polyhydric alcohol ester ethylene oxide adducts, polyethylene glycol monoester, polyethylene glycol diester, higher alcohol ethylene oxide adducts, alkylphenol ethylene oxide adducts, polyoxyethylene polyoxypropylene polyol, etc.

When used alone, they may be those having an HLB value of 12.0 or more, and include, for example, polyoxyethylene polyoxypropylene polyol (SYNPARONIC F68 "trade mark" HLB value=29), polyethylene glycol (10), cetyl ether (BRIJ 56 "trade mark" HLB value=12.9), polyethylene glycol (10) oleyl ether (BRIJ96 "trade mark" HLB value=12.4), polyethylene glycol alkyl allyl ether (RENEX 690 "trade mark", HLB value=13.0), polyethylene glycol (9) p-tert-octylphenol (NP 40 "trade mark", HLB value=13.1), polyethylene glycol sorbitan monolaurate (TWEEN 21 "trade mark", HLB value=13.3; TWEEN 20 "trade mark", HLB value=16.7), polyethylene glycol (9-10) nonylphenol (TRITON "trade mark" N-101, HLB value=13.4), polyethylene glycol (9-10) p-tert-octylphenol (TRITON "trade mark" X-100, HLB value=13.5), polyethylene glycol (12) tridecyl ether (RENEX 30 "trade mark", HLB value=14.5), polyethylene glycol (12-13) p-tert-octylphenol (TRITON "trade mark" X-102, HLB value=14.6), polyethylene glycol sorbitan monostearate (TWEEN 60 "trade mark", HLB value=14.9), polyethylene glycol (20) octyl ether (BRIJ 98 "trade mark",HLB value=15.3), etc. When two or more of them are used, they are not particularly limited so long as the HLB value of the nonionic surfactant mixture calculated according to the above equation is 12.0 or more.

In case a nonionic surfactant having an HLB value under 12.0, lowering of specific immune reaction in the immune reactions is observed, and sufficient sensitivity cannot be obtained.

The final concentration of a nonionic surfactant to be used in this invention in the immune reaction solution is 2 to 15 weight %, preferably 3 to 10 weight %. In case of under 2 weight %, it is impossible to get rid of difference in reactivity between the apoprotein as a standard substance and the tissue factor in the specimen, and when it goes beyond 15 weight %, specific immune reaction is inhibited.

As proteins to be used in this invention having a molecular weight of about 16,000 to about 50,000 and an isoelectric point of 1.0 to 5.0 (or mixtures containing the proteins), there can, for example, be mentioned casein, pepsin, ovoglycoprotein, orosomucoid, etc. When a protein having a molecular weight under about 16,000 is used, nonspecific adsorption increases, and in case of a molecular weight larger than about 50,000, decrease of nonspecific immune reaction is insufficient and lowering of specific immune reaction is observed. Further likewise as for its isoelectric point, when a protein having an isoelectric point larger than 5.0 is added, nonspecific adsorption is increased, and in case its isoelectric point is under 1.0, specific immune reaction is inhibited. The final concentration of the protein in the immune reaction solution is preferably 0.01 to 0.8 weight %. When immunoassay was made using solutions of the protein, for example skim milk in various concentrations, nonspecific reaction cannot sufficiently be inhibited under 0.01 weight %, and when solutions of the protein, for example skim milk were tested for preservation in an refrigerator for one month, precipitates incapable of being redissolved were formed from the skim milk solutions of 0.8 weight % or more, and thus 0.8 weight % or less is preferred in view of their stability in preservation.

A mixture containing the protein can, for example, contain 10 to 60 weight %, preferably 20 to 50 weight % of the above protein as a main component, 30 to 80 weight %, preferably 40 to 60 weight % of a saccharide (e.g., lactose), and as other components a fat (e.g. 0.5 to 2 weight %), ashes (e.g., 5 to 12 weight %), water (e.g., 2 to 8 weight %), etc. A typical example of such mixtures is skim milk. Skim milk contains casein as a protein, but compared with the case of using casein alone, skim milk has characteristics that it has better dispersibility in an immune reaction solution, a better effect to inhibit nonspecific reaction and better perservability at a temperature of 4° C. (precipitate is hard to form). Skim milk derived from any milk can be used in this invention so long as it is defatted milk. One of most typical examples thereof is commercially available skim milk produced by Difco Co. In this invention, the "molecular weight" of the protein means molecular weight measured by an osmotic pressure method. Specifically, the molecular weight of the protein is measured utilizing the fact that when a macromolecule solution and a pure solvent are contacted using as a boundary face a semipermeable membrane through which molecules of the solvent can freely permeate but the eluted macromolecule cannot, the difference in osmotic pressure of the both liquids becomes a parameter of the molecular weight of the macromolecule. In this invention, the molecular weight of the protein is a value measured at 4° C. using a 6.66M urea solution. Further, "isoelectric point" means a value measured by a chromatofocusing method wherein a protein is separated in accordance with its isoelectric point, and specifically, means a value measured using a column (0.5 cm $\phi \times 45$ cm) packed with PBE 94 (Poly Buffer Exchanger 94 produced by Pharmacia Co.) gel and 0.025M imidazole-hydrochloric acid (pH 7.4) as an eluent.

In the method of this invention, when the surfactant and the protein are made to coexist in a concentration of 2 to 15 weight % and in a final concentration of 0.01 to 0.8 weight %, respectively, in the immune reaction solution (buffer solution), the above-mentioned respective effects are more effectively exhibited and at the same time a coexistence effect of remarkable improvement of measurement error is obtained.

(C) Immunoassay method:

Hereafter, description is made on a specific means to measure the human tissue factor in a specimen with utilization of immune reaction in this invention.

The method for immunological measurement in this invention can be carried out by a sandwich method based on EIA, FIA, CLIA, RIA or the like. Description is made herein on an EIA sandwich method preferably used for convenience sake, but the method of this invention is not limited thereto.

Sandwich methods roughly include a one step sandwich method and a two step sandwich method. For example, the one step sandwich method is a method which comprises subjecting a specimen containing an antigen to be measured, a solid phase antibody wherein the antibody is immobilized on an insoluble carrier and a labeled antibody wherein the antibody is labeled with an enzyme to antigen-antibody reaction in the same reaction system to form a solid phase antibody-antigen-labeled antibody complex, and after washing operation, measuring the quantity of the labeling substance. In this occasion, the specimen, the solid phase antibody and the labeled antibody may be made to exist at the same time and reacted, or it is also possible to react the specimen and the solid phase antibody first and then add the labeled antibody to carry out reaction. It is further possible to add the solid phase antibody after reaction of the specimen with the labeled antibody. Anyway, the requisite is to form the solid phase antibody-antigen-labeled antibody complex in the same reaction system before the washing operation. On the other hand, the two step sandwich method is a method which comprises reacting first the specimen and the solid phase antibody to form a solid phase antibody-antigen complex, after removal of the specimen and washing, adding the labeling substance to form the solid phase antibody-antigen-labeled antibody complex, and then after washing operation, measuring the quantity of the labeling substance.

In this invention, a very small quantity of the tissue factor can be measured in high sensitivity, accurately, with only a small measurement error, in a short time and easily, in any of the one step sandwich method and the two step sandwich method, by making the surfactant and the protein or mixture containing the protein to coexist in the immune reaction solution.

In case of the two step sandwich method, the surfactant and the protein can be made to coexist in at least one of the immune reaction solution for the first reaction and the immune reaction solution for the second reaction, but most preferably, they are made to coexist in both reaction solutions.

Solvents to be used in the above immune reaction may include usual various ones which do not have a bad influence on the reaction. It is preferred to use buffer solutions having a pH of the order of 6.0 to 8.0 such as, for example, phosphate buffer, Tris-hydrochloric acid buffer and acetate buffer.

There is no particular limitation about the immune reaction temperature condition in the measurement so long as it does not denature the properties of the protein used and does not strikingly inhibit the specific immune reactions, but reaction may be carried out under a temperature condition of generally 50° C. or less, preferably of the order of about 4 to 45° C. for about 5 minutes to about 5 hours.

The kit used in the above measurement method in this invention is composed of (a) a first antibody (solid phase antibody),
(b) a second antibody (labeled antibody),
(c) a buffer solution,
(d) a washing solution and
(e) in case of use of an enzyme-labeled antibody as the second antibody, a substrate for measuring enzyme activity and a reaction-discontinuing agent.

In the kit of this invention, the first antibody of (a) is a monoclonal antibody specifically recognizing the apoprotein of the human tissue factor and immobilized on an insoluble carrier, and the second antibody of (b) is a labeled monoclonal antibody specifically recognizing the apoprotein of the human tissue factor and having a recognition site different from that by the first antibody.

Further in the kit of this invention, as themselves or in solution state(s) thereof are further combined (i) at least one nonionic surfactant having an HLB (Hydrophilic-lipophilic balance) value of 12 or more, and
(ii) a protein having a molecular weight of about 16,000 to about 50,000 and an isoelectric point of 1.0 to 5.0, or a mixture containing the protein.

The nonionic surfactant of the above (i) and the protein or the mixture containing the protein of (ii) may constitute the kit in combination of themselves, or may be combined in solution states. In case of "solution states", they are dissolved, preferably in portions of the buffer solution of the above (c) as a solvent, respectively to compose the kit. In this occasion, the concentration of the nonionic surfactant in a solution state may be in such a range that the concentration at the final use form is in the above range, and thus may be, in the kit, a concentration more concentrated than the above range. Further, the protein or its mixture can likewise be in the concentration at the final use form or its concentrated solution.

Washing solution (d) may be one usually used as a washing solution in immunoassay.

Examples thereof are physiological saline, phosphate buffer, Tris-hydrochloric acid buffer and a mixed solution thereof. There may further be added to such a washing solution a nonionic surfactant such as TRITON X-100, TWEEN 20 or BRIG 35, or an ionic surfactant such as sodium dodecyl sulfate.

Further, it is possible to add to buffer solution (c) and/or washing agent (d) a protein such as bovine serum albumin or ovalbumin, serum of an animal, a saccharide, a stabilizer, an antiseptic, etc.

The specimen in this invention means a sample containing a tissue factor as an antigen with which an antibody specifically recognizing anti-human tissue apoprotein in this invention can immunely react.

Such tissue factors as antigens include not only the human tissue factor but the tissue factors of other animals which can crossly react with the antibody.

Further, there is no particular limitation on the sample so long as in case of an animal, e.g. human being, it contains the human tissue factor, but specifically, there can be mentioned humors in a solution state such as urine, blood (plasma and serum), articular fluid, sputum and sweat. Blood and urine are preferred among them in view of easiness of obtention as a sample, etc. The sample may be a supernatant obtained by homogenizing a tissue in a solid state such as brain, lung, kidney, cardiac muscle, digestive apparatus, placenta, blood vessel, angioendothelium or blood cells.

However, this invention is most suitable for measurement of the human tissue factor in a human specimen, particularly human serum or human plasma.

DETAILED DESCRIPTION OF THE PREFERRED EMBODIMENTS

Figure 1:
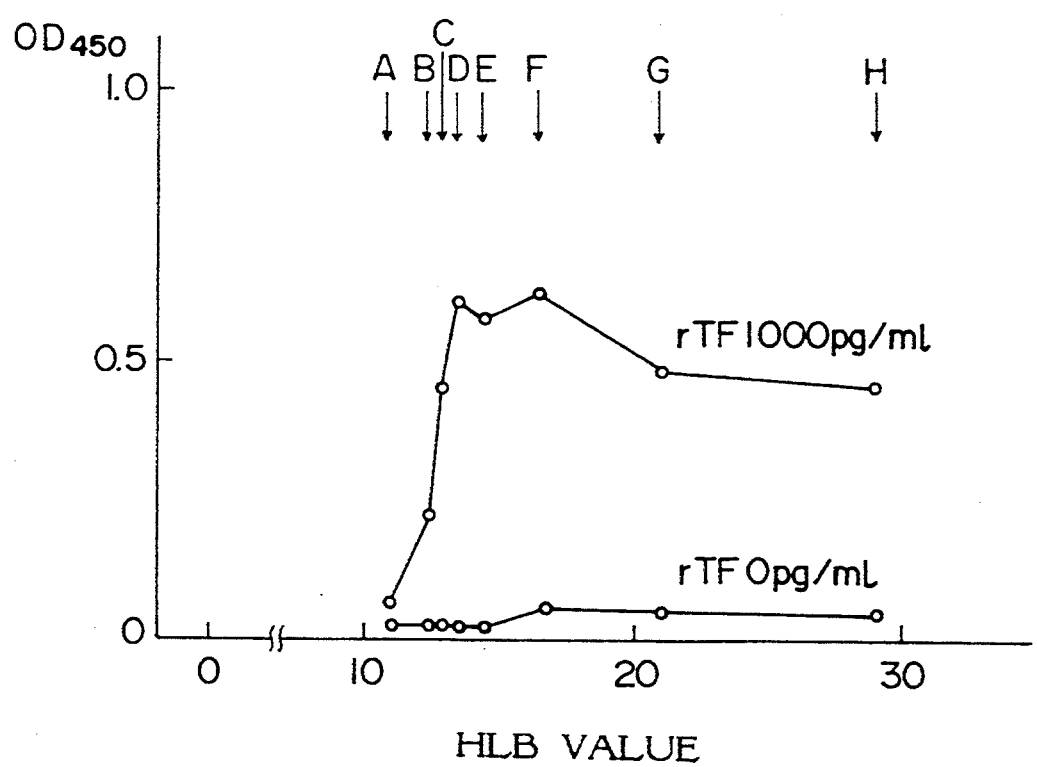
FIG. 1 shows the relations between the HLB values of the nonionic surfactants and absorbances on the standard substance obtained according to the method of this invention.

Thus according to the immunological measurement method of this invention, a very small quantity of the tissue factor in a specimen such as, for example, a clinical sample (a humor such as plasma, serum or urine, or the like) can be quantitatively determined by immune reactions in a solution in high sensitivity, accurately, with only a small measurement error, in a short time and by convenient operations.

The measured values of a tissue factor by the immunological measurement method and measurement kit of this invention are useful for diagnosis and monitoring treatment of thrombotic diseases, angiopathic diseases, neoplastic diseases and the like, etc.

EXAMPLE

This invention is described in detail below according to examples. In the examples, % means weight %.

EXAMPLE 1

(1) Preparation of beads immobilizing an anti-human tissue factor apoprotein monoclonal antibody A solution in 0.1M carbonate buffer (pH 9.5) of monoclonal antibody TF9-6B4 (disclosed in Japanese Tokuhyohei No. 503438/1989) having a binding site to the region of the 146th to 167th amino acid residues of the human tissue factor apoprotein in an concentration of 20 $\mu$g/ml was prepared. Polystyrene beads having a mirror-like surface (Immunochemical Immunobeads, surface center line average roughness (Ra) measured using Surfcom 570A (produced by Tokyo Seimitsui Co., Ltd.) (Ra): 1.3 $\mu$m) were immersed therein and allowed to stand at 4° C. for 17 hours. Beads were washed three times with 50 mM Tris hydrochloric acid —0.1M NaCl (pH 7.4) (hereafter abbreviated TBS) and then allowed to stand in 1% BSA-TBS (pH 7.4) at room temperature for 3 hours. The beads were washed again three times with TBS to obtain beads immobilizing the monoclonal antibody. The beads were preserved in TBS at 4° C. until use.

(2) Preparation of a peroxidase-labeled anti-human tissue factor apoprotein monoclonal antibody Into a solution in 0.5 ml of PBS of 635 $\mu$g of monoclonal antibody TF8-5G9 having a binding site to the region of the 26th to 49th amino acid residues of the human tissue factor apoprotein (disclosed in Japanese Tokuhyohei No. 503438/1989) was added dropwise at 25° C. with stirring 10.6 $\mu$l of a DMF solution of succinimidyl-4-(N-maleimidomethyl)cyclohexane carbonate (SMCC) (10 mg/ml). The resultant reaction mixture was stirred for 45 minutes and centrifuged at 3000 rpm for 10 minutes to obtain a supernatant. This supernatant was subjected to gel filtration by HPLC (column: TSK Gel 3000 SW) using 0.1M phosphate buffer solution (pH 6.0) as an eluent to obtain a maleimidated monoclonal antibody.

176.4 $\mu$l of a DMF solution of S-acetylmercaptosuccinic anhydride (60 mg/ml) was gradually dropwise added at 25° C. to 14.3 ml of a solution of 143 mg of peroxidase (Toyobo) in 0.1M phosphate buffer (pH 6.0) with stirring to carry out reaction for 60 minutes. To the resultant solution were added 5.72 ml of 0.1M Trishydrochloric acid buffer (pH 7.0), 1.14 ml of 0.1M EDTA solution (pH 7.0) and 11.44 ml of 1M hydroxylamine solution (pH 7.0), followed by stirring at 30° C. for 5 minutes. The resultant solution was put in a dialysis tube and dialyzed at 4° C. for two days and nights against 0.1M phosphate buffer (pH 6.0)—5 mM EDTA as the outer liquid to obtain a solution of peroxidase into which thiol groups were introduced.

The solution of the maleimidated monoclonal antibody and 445 $\mu$l of the solution of the thiolized peroxidase (3.57 mg/ml) thus obtained were mixed, and the mixture was concentrated by ultrafiltration to about 140 $\mu$l, and subjected to reaction at 4° C. for 48 hours. The reaction solution was subjected to gel filtration by HPLC (column: TSK Gel 3000 SW) using PBS (pH 7.2) as an eluent to obtain a peroxidase-labeled monoclonal antibody. The mole ratio of the antibody of the labeled antibody to the peroxidase was 1:3.3.

(3) Preparation of a calibration curve on the human tissue factor

Solutions of recombinant human tissue factor apoprotein in concentrations of 0, 15, 31, 63, 125, 250, 500 and 1000 Pg/ml were prepared using, as a diluting buffer, 50 mM Tris HCl—0.1M NaCl—0.5% BSA—3%

TRITON X-100—0.1% skim milk (pH 7.4), and 0.4 ml portions of them were put into polypropylene-made tubes, respectively (N=2). One of the beads immobilizing the monoclonal antibody described in the above item (1) was put into each tube, and the mixture was subjected to incubation at 37° C. for 120 minutes.

After three times washing with a 0.05% solution of TWEEN 20 in 50 mM Tris hydrochloric acid—0.1M NaCl (pH 7.4) (hereafter abbreviated as TBS-T), 0.4 ml portions of the peroxidase-labeled monoclonal antibody prepared in the above item (2) adjusted to an antibody concentration of 1 μg/ml with the above diluting buffer were added, and the mixtures were subjected to incubation at 37° C. for 60 minutes.

After three times washing with TBS-T, 0.4 ml portions of 2.5 mM $H_2O_2$—0.025% 3,3′,5,5′-tetramethylbenzidine solution were added as a color former, and the mixtures were subjected to incubation at 37° C. for 30 minutes. Thereafter, 1 ml of 1N sulfuric acid was put into each tube to discontinue the coloring reaction, and absorbance was measured at 450 nm. From absorbance at each concentration obtained, a coefficient of variation (CV) as an index of a measurement error was calculated by the following equation, and the results were shown in Table 1.

CV (%)={(standard deviation)/(average value)}×100

As comparative examples, on each of the case where TRITON X-100 was removed from the above diluting buffer, the case where skim milk was removed therefrom, and the case where both of TRITON X-100 and skim milk were removed, the absorbance of the apoprotein at each concentration was measured in the same operation as above, and a coefficient of variation was calculated. The resultant values were shown in Table 1 as comparative values.

was put into each tube, and the mixture was subjected to incubation at 37° C. for 120 minutes.

After three times washing with TBS-T, 0.4 ml portions of solutions obtained by dissolving portions of the labeled antibody prepared in item (2) of Example 1 in an antibody concentration of 1 μg/ml in the above diluting buffers, respectively were added thereto so that the respective surfactants corresponded, and the resultant mixtures were subjected to incubation at 37° C. for 60 minutes.

After three times washing with TBS-T, 0.4 ml portions of 2.5 mM $H_2O_2$—0.025% 3,3′,5,5′-tetramethylbezidine solution were added as a color former, the mixtures were subjected to incubation at 37° C. for 30 minutes, and 1 ml portions of 1N sulfuric acid were added to discontinue the coloring reactions. Thereafter, absorbances were measured at 450 nm.

The HLB values of the nonionic surfactants, and absorbances in 0 Pg/ml and 1000 Pg/ml of a standard substance (γTF) at 450 nm were shown in FIG. 1.

As is apparent from FIG. 1, when the HLB value of the nonionic surfactant contained in the immune reaction solution was under 12.0, lowering of absorbance took place and sufficient measurement sensitivity could not be obtained.

EXAMPLE 3

Measurement of the human tissue factor in normal human plasma with change of concentration of Triton X A normal human plasma specimen (B) was 4-fold diluted using, as a diluting buffer, 0.5% BSA—50 mM Tris hydrochloric acid—0.1M NaCl (pH 7.4) containing 0.1% skim milk and TRITON X-100 in one of the predetermined concentrations (0, 1, 2, 3, 5, 10, 15 and 20%). The resultant specimen dilutions were put in polypropylene-made tubes in quantities of 0.4 ml portions, respectively (N=2). One of the beads immobiliz-

TABLE 1

| | Triton X-100 (%) | Skim milk (%) | Standard deviation value | | | | | | | |
|---|---|---|---|---|---|---|---|---|---|---|
| | | | 0 Pg/ml | 15 Pg/ml | 31 Pg/ml | 63 Pg/ml | 125 Pg/ml | 250 Pg/ml | 500 Pg/ml | 1000 Pg/ml |
| Present invention | 3.0 | 0.1 | 3.0 | 0.0 | 1.6 | 2.3 | 2.8 | 3.9 | 1.3 | 2.9 |
| Comparative example | 3.0 | 0 | 12.3 | 15.4 | 12.1 | 29.4 | 36.8 | 11.5 | 10.4 | 7.5 |
| | 0 | 0.1 | 5.4 | 8.0 | 7.1 | 4.3 | 5.1 | 4.0 | 1.5 | 2.9 |
| | 0 | 0 | 54.5 | 25.1 | — | — | — | — | — | 3.8 |

"—" in the Table means that the test was NOT DONE.

As is apparent from Table 1, when Triton X-100 and skim milk were made to coexist in the immune reaction solution, which is the method of the present invention, a coefficient of variation, i.e. a measurement error at each concentration became remarkably small.

EXAMPLE 2

Relation between HLB values of nonionic surfactants and absorbances on a standard substance A normal human plasma specimen (A) was 4-fold diluted using, as a diluting buffer, 0.5% BSA—50 mM Tris hydrochloric acid—0.1M NaCl (pH 7.4) containing 0.1% skim milk and one of the various nonionic surfactants (A to H) having an HLB value shown in FIG. 1 in a concentration of 5%. The resultant specimen dilutions were put in polypropylene-made tubes in quantities of 0.4 ml portions, respectively. One of the beads immobilizing the antibody described in item (1) of Example 1 ing the antibody described in item (1) of Example 1 was put into each tube, and the mixture was subjected to incubation at 37° C. for 120 minutes.

After three times washing with TBS-T, 0.4 ml portions of solutions obtained by dissolving portions of the labeled antibody prepared in item (2) of Example 1 in an antibody concentration of 1 μg/ml in the above diluting buffers, respectively were added thereto so that the respective Triton X-100 concentrations corresponded, and the resultant mixtures were subjected to incubation at 37° C. for 60 minutes.

After three times washing with TBS-T, 0.4 ml portions of 2 5 mM $H_2O_2$—0.025% 3,3′,5,5′-tetramethylbenzidine solution were added as a color former, the mixtures were subjected to incubation at 37° C. for 30 minutes, and 1 ml portions of 1N sulfuric acid were added to discontinue the coloring reactions. Thereafter, absorbances were measured at 450 nm.

On the other hand, using as a standard substance the apoprotein used in item (3) of Example 1 and the same diluting buffers as above, calibration curves corresponding to the respective concentrations of TRITON X-100 were made by the same operation as above. Then, using the calibration curves on the corresponding TRITON X-100 concentrations, concentrations of the human tissue factor were determined from absorption strengths at 450 nm measured on the diluted specimens, obtained as above. The concentrations of the human tissue factor obtained against the respective TRITON X-100 concentrations were shown in FIG. 2.

Figure 2:
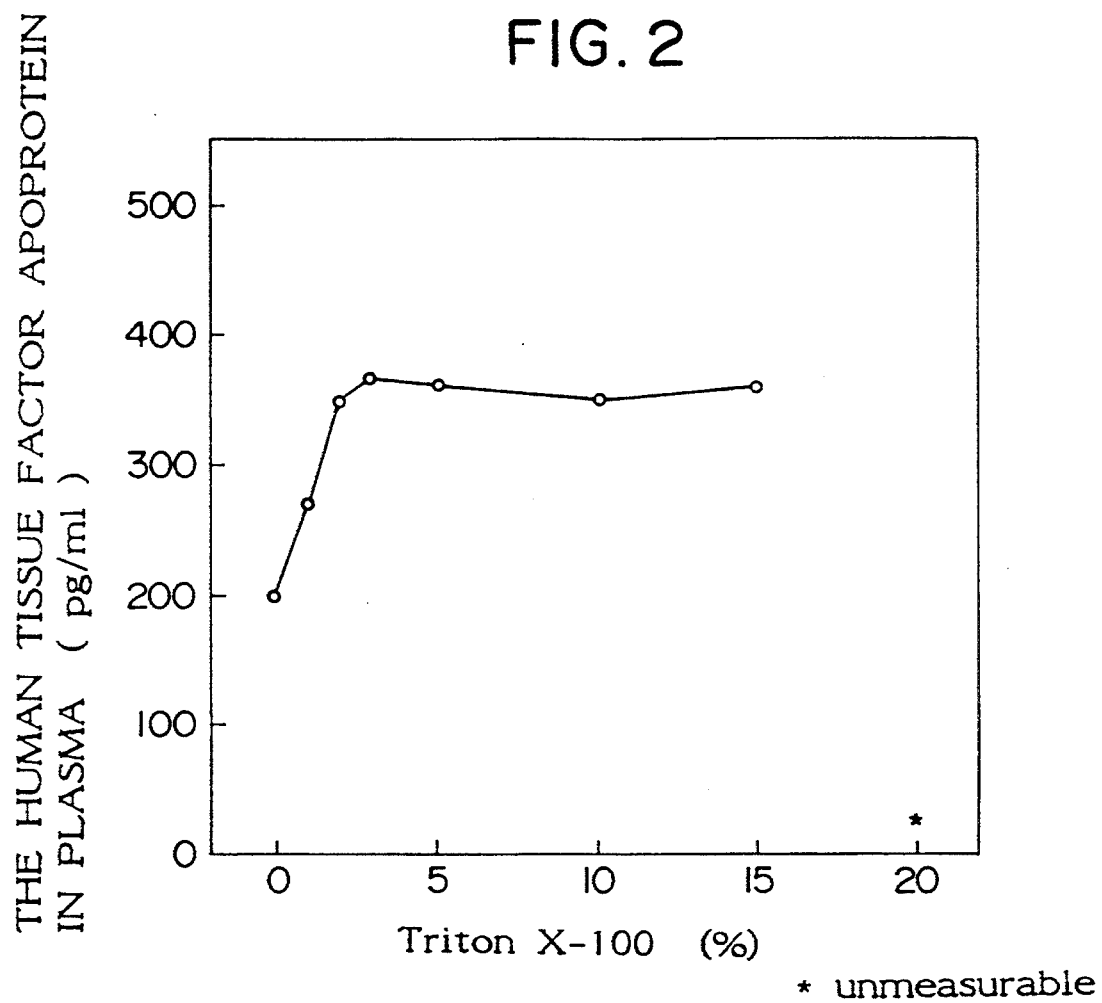
FIG. 2 shows the results of measurements of the human tissue factor in normal human plasma in the case where the content of TRITON X-100 was changed in the presence of skim milk.

As is apparent from FIG. 2, the measured values were the highest and constant in 2 to 15% of Triton X-100.

EXAMPLE 4

Measurement error and measurement sensitivity with change of concentration of skim milk 0 and 1000 Pg/ml solutions of recombinant human tissue factor apoprotein were prepared using as a diluting buffer 0.5% BSA—50 mM Tris hydrochloric acid—0.1M NaCl (pH 7.4) containing 3.0% Triton X-100 and skim milk in one of the predetermined concentrations (0, 0.005, 0.01, 0.02, 0.1, 0.8 and 1.0%). 0.4 ml portions of the resultant solutions were put into polypropylene-made tubes (N=2). One of the beads immobilizing the antibody described in item (1) of Example 1 was put into each tube, and the mixture was subjected to incubation at 37° C. for 120 minutes.

After three times washing with TBS-T, 0.4 ml portions of solutions obtained by dissolving portions of the labeled antibody prepared in item (2) of Example 1 in an antibody concentration of 1 μg/ml in the above diluting buffers, respectively were added thereto so that the respective skim milk concentrations corresponded, and the resultant mixtures were subjected to incubation at 37° C. for 60 minutes.

After three times washing with TBS-T, 0.4 ml portions of 2 5 mM $H_2P_2$—0.025% 3,3',5 5'-tretramethylbenzidine solution were added as a color former, the mixtures were subjected to incubation at 37° C. for 30 minutes, and 1 ml portions of 1N sulfuric acid were added to discontinue the coloring reactions. Thereafter, absorbances were measured at 450 nm. From these absorbances were calculated coefficients of variation (CV) and S/N ratios ($OD_{450}$ value at 1000 Pg/ml apoprotein/$OD_{450}$ value at 0 Pg/ml apoprotein) as an index of sensitivity at the respective skim milk concentrations.

TABLE 2

| | | Skim milk concentration (%) | | | | | |
|---|---|---|---|---|---|---|---|
| | | 0 | 0.005 | 0.01 | 0.02 | 0.1 | 0.8 |
| 0 | $OD_{450}$ | 0.055 | 0.052 | 0.044 | 0.041 | 0.034 | 0.035 |
| Pg/ml | CV (%) | 5.2 | 8.1 | 0.0 | 3.1 | 2.2 | 1.8 |
| 1000 | $OD_{450}$ | 0.388 | 0.405 | 0.425 | 0.405 | 0.428 | 0.400 |
| Pg/ml | CV (%) | 0.1 | 8.3 | 2.5 | 3.5 | 3.5 | 5.0 |
| S/N ratio | | 7.1 | 7.8 | 9.7 | 9.9 | 12.6 | 11.4 |

As is apparent from Table 2, when Triton X-100 was made to coexist in a concentration of 3%, both CV and SN ratio were good at skim milk concentrations between 0.01% and 0.8%.

EXAMPLE 5

Effect by use of both Triton X-100 and skim milk together in normal human plasma measurement Normal human plasma specimens C and D were 4-fold diluted respectively, using, as a diluting buffer, 0.5% BSA—50 mM Tris hydrochloric acid—0.1M NaCl (pH 7.4) containing 3.0% Triton X-100 and skim milk in one of concentration combinations of 0%–0.1%, 0.1%–3.0% and 0.1%–3.0%. The resultant specimen dilutions were put in polypropylene-made tubes in quantities of 0.4 ml portions, respectively (N=2). One of the beads immobilizing the antibody described in item (1) of Example 1 was put into each tube, and the mixture was subjected to incubation at 37° C. to 120 minutes.

After three times washing with TBS-T, 0.4 ml portions of solutions obtained by dissolving portions of the labeled antibody prepared in item (2) of Example 1 in an antibody concentration of 1 μg/ml in the above diluting buffers, respectively were added thereto so that the respective concentration combinations corresponded, and the resultant mixtures were subjected to incubation at 37° C. for 60 minutes.

After three times washing with TBS-T, 0.4 ml portions of 2 5 mM $H_2O_2$—0.025% 3,3',5,5'-tetramethylbenzidine solution were added as a color former, the mixtures were subjected to incubation at 37° C. for 30 minute, and 1 ml portions of 1N sulfuric acid were added to discontinue the coloring reactions. Therefore, absorbances were measured at 450 nm.

On the other hand, using as a standard substance the apoprotein used in item (3) of Example 1 and the same diluting buffers as above, calibration curves corresponding to the respective concentration combinations of TRITON X-100 and skim milk were made by the same operation as above. Then, using the calibration curves on the corresponding concentration combinations, concentrations of the human tissue factor were determined from absorption strengths at 450 nm measured on the diluted specimens, obtained as above. In Table 3 were shown the concentrations of the human tissue factor and coefficients of variation (CV) obtained against the respective concentration combinations.

TABLE 3

| | TRITON X-100 (%) | Skim milk (%) | Normal human plasma A | | Normal human plasma B | |
|---|---|---|---|---|---|---|
| | | | Apoprotein Pg/ml | CV (%) | Apoprotein Pg/ml | CV (%) |
| This invention | 3.0 | 0.1 | 368 | 1.1 | 262 | 1.3 |
| Comparative example | 3.0 | 0 | 270 | 10.8 | 250 | 15.5 |
| | 0 | 0.1 | 200 | 15.1 | 100 | 11.0 |

As is apparent from Table 3, when the specimens were measured in coexistence of TRITON X-100 and skim milk, as a case of this invention, the human tissue factor could be measured with only a small measurement error (coefficient of variation) and accurately.

EXAMPLE 6

Relation between the surface center line roughness of immobilizing beads and S/N ratio 10 ml of a solution in 0.1M carbonate buffer (pH 9.5) of monoclonal antibody TF9-6B4 described in item (1) of Example 1 in a concentration of 20 μg/ml was prepared. This solution was divided into 5 ml portions, to one of the resultant two solutions were added 30 polystyrene beads having a mirror-like surface (Immunobeads produced by Immunochemical Co., surface center line average roughness (Ra) measured by Surfcom 570A (produced by Tokyo Seimitsu Co., Ltd.) : 1.3 μm), to the other solution were added, as a comparative example, 30 polystyrene beads having a mirror-unlike surface (#80 beads produced by Sekisui Co., Ltd., Ra measured in the same manner as above: 3.9 μm), and both these beads were allowed to stand at 4° C. for 20 hours. After washing the beads three times with TBS, they were allowed to stand at room temperature for 3 hours in 1% BSA-TBS (pH 7.4). These beads were again washed three times with TBS to obtain an antibody (A) immobilized on the polystyrene beads having a mirror-like surface as an immobilized antibody of this invention and an antibody (B) immobilized on the polystylene beads having a mirror-unlike surface as an immobilized antibody of the comparative example.

0 and 1000 Pg/ml solutions of the apoprotein were prepared in the same way as in item (3) of Example 1, and absorbance at 450 nm in each concentration of the apoprotein was measured on each of immobilized antibodies (A) and (B) in the same way as in the above item (3). S/N ratio ($OD_{450}$ value at 1000 Pg/ml apoprotein/$OD_{450}$ value at 0 Pg/ml apoprotein) was calculated as an index of sensitivity on each immobilized antibody. These results are shown in Table 4.

TABLE 4

| Beads | $OD_{450}$ | | |
|---|---|---|---|
| (Surface center line roughness) | 0 Pg/ml | 1000 Pg/ml | S/N ratio |
| Present invention | Beads A having a mirror-like surface (1.3 μm) | 0.021 | 0.555 | 26.4 |
| Comparative example | Beads B having a mirror-unlike surface (3.9 μm) | 0.041 | 0.303 | 7.4 |

As is apparent from Table 4, the beads of this invention having a mirror-like surface made low background and high S/N possible.

EXAMPLE 7

Preparation of a calibration curve by a one step sandwich method 0, 15, 31, 63, 125, 250, 500, 1000 and 2000 Pg/ml solutions of recombinant human tissue factor apoprotein in a diluting buffer 0.5% BSA—3% Triton X-100—0.1% skim milk—50 mM Tris hydrochloric acid—0.1M NaCl (pH 7.4) were prepared, and 0.2 ml portions of them were put in polypropylene-made tubes, respectively. Into the respective tubes were added 0.2 ml portions of solutions obtained by dissolving the peroxidase-labeled monoclonal antibody prepared in item (2) of Example 1 in the above respective diluting buffers to an antibody concentration of 1 μg/ml, and the mixtures were stirred. Thereafter, one of the beads immobilizing the monoclonal antibody described in the above item (1) was put in each tube, and the mixture was subjected to incubation at 37° C. for 120 minutes.

After three times washing with TBS-T, 0.4 ml portions of 2.5 mM $H_2O_2$—0.025% 3,3',5,5'-tetramethylbenzidine solution as a color former were added, the resultant mixtures were subjected to incubation at 37° C. for 30 minutes, coloring reactions were discontinued with addition of 1 ml portions of 1N sulfuric acid, and then absorbances were measured at 450 nm. The resultant calibration curve was shown in FIG. 3.

Figure 3:
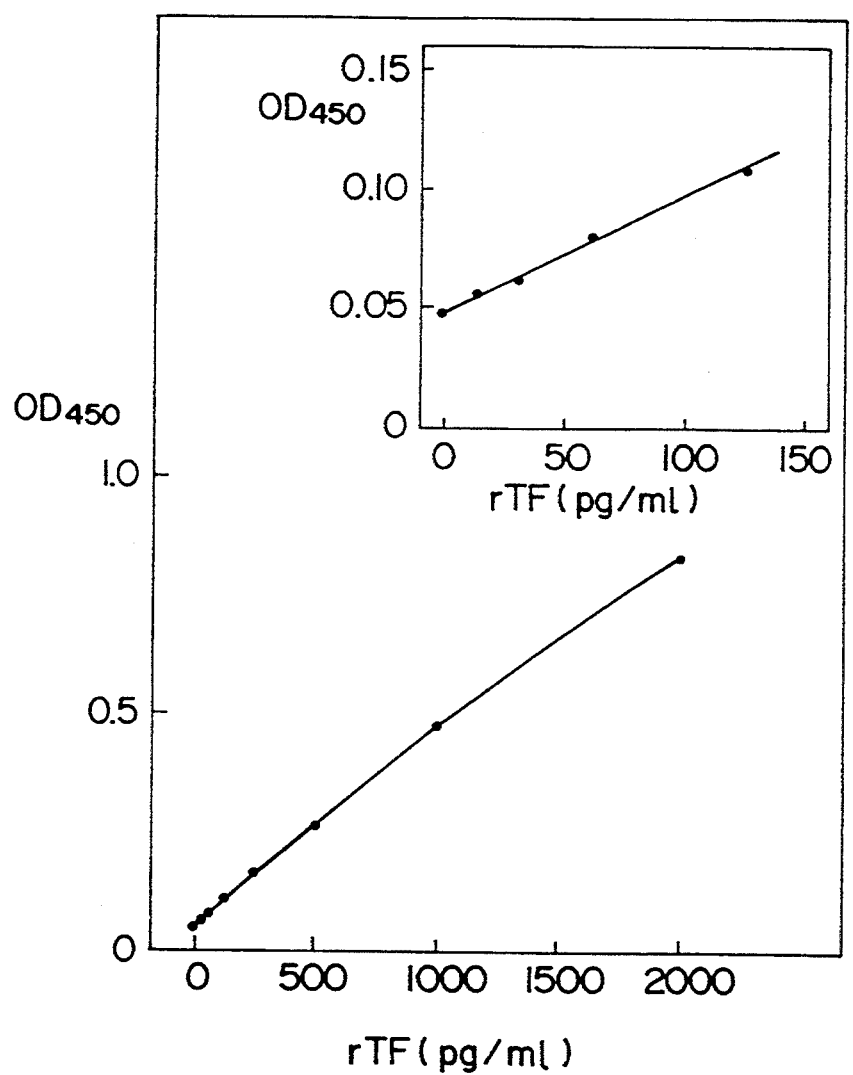
FIG. 3 shows a calibration curve for a one step sandwich method by the method of this invention.

As is apparent from FIG. 3, the one step sandwich method of this invention gives a high sensitivity of 15 Pg/ml and makes obtention of a good calibration curve possible.

EXAMPLE 8

Measurement of specimens

Plasma specimens or urine specimens shown in Table 5 were 4-fold diluted, respectively, using, as diluting buffer, 3% Triton X-100—0.1% skim milk—0.5% BSA—50 mM Tris hydrochloric acid—0.1M NaCl (pH 7.4). 0.4 ml portions of the resultant specimen dilutions were put in polypropylene-made tubes (N=2), respectively, one of the beads immobilizing the antibody described in item (1) of Example 1 was put in each tube, and the resultant mixtures were subjected to incubation at 37° C. for 120 minutes.

After three times washing with TBS-T, 0.1 ml portions of solutions obtained by dissolving the labeled antibody prepared in item (2) of Example 1 in the above respective diluting buffers were added, and the mixtures were subjected to incubation at 37° C. for 60 minutes.

After three times washing with TBS-T, 0.4 ml portions of 2.5 mM $H_2O_2$—0.025% 3,3',5,5'-tetramethylbenzidine solution as a color former were added, the resultant mixtures were subjected to incubation at 37° C. for 30 minutes, and 1 ml portions of 1N sulfuric acid were added to discontinue the coloring reactions. Thereafter, absorbances were measured at 450 nm.

Figure 4:
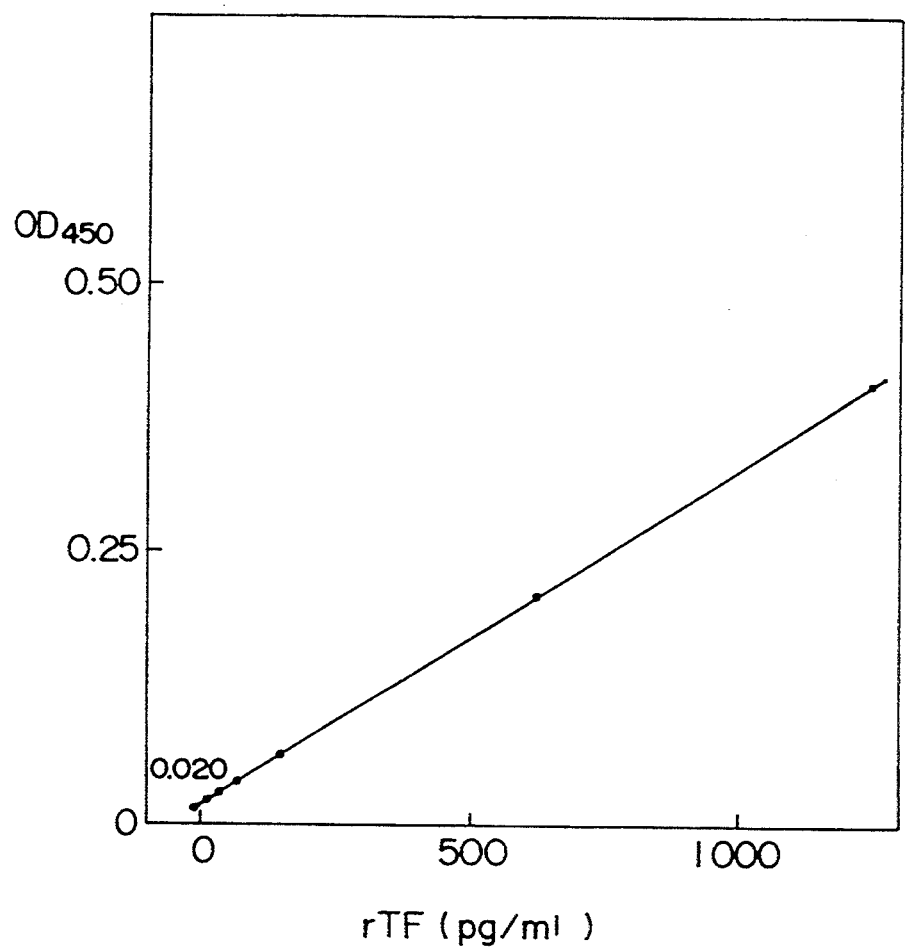
FIG. 4 shows a calibration curve for quantitatively determining the human tissue factor in human plasma by the method of this invention.

On the other hand, the same procedure as above was carried out using as a standard substance the apoprotein used in item (3) of Example 1 and the same diluting buffer as above to prepare a calibration curve. The resultant calibration curve is shown in FIG. 4.

Using this calibration curve, the concentrations of the human tissue factor apoprotein in the plasma specimens were determined from the absorption strengths of the respective specimens at 450 nm obtained above, and the results are shown in Table 5.

TABLE 5

| | Specimen | $OD_{450}$ | Apoprotein concentration (Pg/ml) |
|---|---|---|---|
| Plasma | Normal human being A | 0.041 | 320 |
| | Normal human being B | 0.044 | 360 |
| | Normal human being C | 0.031 | 180 |
| | DIC patient | 0.078 | 820 |
| | Diabetic nephritis A | 0.081 | 880 |
| | Diabetic nephritis B | 0.071 | 760 |
| | Pulmonary infarction | 0.054 | 500 |
| Urine | Normal human being | 0.026 | 80 |
| | Leukemia patient A | 0.040 | 280 |
| | Leukemia patient B | 0.066 | 640 |

We claim:

1. In a method for immunologically measuring the presence or concentration of apoprotein of human tissue factor contained in a sample, which method comprises the steps of (1) forming in a buffer solution a ternary complex of (a) a first monoclonal antibody which specifically binds to the apoprotein and is immobilized on a solid carrier insoluble in the buffer solution, the solid carrier having a smooth surface and a center line average surface roughness of 1.5 μm or less, (b) the apoprotein and (c) a labeled second monoclonal antibody which specifically binds to the apoprotein at a different site from the binding site of the first monoclonal antibody, and (2) measuring the amount of labeled second monoclonal antibody in the ternary complex to determine the presence or concentration of apoprotein in the sample, the improvement comprising employing as the buffer solution a buffer solution
    (i) containing in a concentration of 2 to 15 weight % at least one nonionic surfactant having a hydrophilic lipophilic balance (HLB) value within a range of 12 to 30, and
    (ii) containing a protein which inhibits non-specific adsorption having a molecular weight of about 16,000 to about 50,000 and an isoelectric point of 1.0 to 5.0, wherein the buffer solution provides a final concentration of 0.01 to 0.8 weight % of the protein in an immune reaction solution.

2. The method according to claim 1, wherein the ternary complex is formed by contacting the first monoclonal antibody, the apoprotein and the labeled second monoclonal antibody in the buffer solution at the same time.

3. The method according to claim 1, which comprises in order the steps of:
    (1) contacting the first monoclonal antibody with the apoprotein in the buffer solution to form an immuno-complex of the first monoclonal antibody and the apoprotein,
    (2) separating the resultant immuno-complex from unreacted materials with a washing agent,
    (3) contacting the resultant immuno-complex with the labeled second monoclonal antibody in the buffer solution to form the ternary complex of the first monoclonal antibody, the apoprotein and the labeled second monoclonal antibody,
    (4) separating the resultant ternary complex from unreacted labeled second monoclonal antibody with a washing agent, and
    (5) measuring the amount of labeled second monoclonal antibody in the ternary complex to determine the presence or concentration of apoprotein of human tissue factor in the sample.

4. The method according to claim 1, wherein the first and second monoclonal antibodies neutralize the binding ability of human tissue factor to coagulation factor VII/VIIa.

5. The method according to claim 1, wherein one of the first or second monoclonal antibodies specifically binds to the following amino acid sequence (I), and the other monoclonal antibody specifically binds to the following amino acid sequence (II):

EPKPVNQVYTVQISTKSGDWKSKC    (I), and

VFGKDLIYTLYYWKSSSSGKKT    (II).

6. The method according to claim 1, wherein each monoclonal antibody is independently a complete antibody, an Fab' fragment or an F(ab')2 fragment.

7. The method according to claim 1, wherein the first monoclonal antibody is a complete antibody, an Fab' fragment or an F(ab')2 fragment.

8. The method according to claim 1, wherein the labeled second monoclonal antibody is a complete antibody, an Fab' fragment or an F(ab')2 fragment.

9. The method according to claim 1, wherein the buffer solution contains a concentration of 3 to 10 weight % of said at least one nonionic surfactant having an HLB value within a range of 12 to 30.

10. The method according to claim 1, wherein the nonionic surfactant is polyethylene glycol mono-alkylphenol ether.

11. The method according to claim 1, wherein the protein comprises skim milk.

12. The method according to claim 1, wherein the insoluble solid carrier comprises beads.

13. The method according to claim 1, wherein the sample is human serum or human plasma.

14. The method according to claim 1, wherein the protein is at least one selected from the group consisting of casein, pepsin, ovoglycoprotein and orosomucoid.

15. In a kit for immunologically measuring the presence or concentration of apoprotein of human tissue factor contained in a sample which kit includes
  (a) a first monoclonal antibody which specifically binds to the apoprotein and is immobilized on a solid carrier insoluble in a buffer solution, the solid carrier having a smooth surface and a center line average surface roughness of 1.5 μm or less,
  (b) a labeled second monoclonal antibody which specifically binds to the apoprotein at a different site from the binding site of the first monoclonal antibody,
  (c) a buffer solution
  (d) a washing solution, and
  (e) in a kit where an enzyme-labeled antibody is used as the labeled second monoclonal antibody, a substrate for measuring the enzyme activity and a reaction stopping agent,
  the improvement comprising employing as the buffer solution a buffer solution
    (i) containing in a concentration of 2 to 15 weight % at least one nonionic surfactant having an HLB value within a range of 12 to 30, and
    (ii) containing a protein which inhibits non-specific adsorption having a molecular weight of about 16,000 to about 50,000 and an isoelectric point of 1.0 to 5.0, wherein the buffer solution provides a final concentration of 0.01 to 0.8 weight % of the protein in an immune reaction solution.

16. The kit according to claim 15, wherein the first and second monoclonal antibodies neutralize the binding ability of human tissue factor to coagulation factor VII/VIIa.

17. The kit according to claim 15, wherein one of the first or second monoclonal antibodies specifically binds to the following amino acid sequence (I), and the other monoclonal antibody specifically binds to the following amino acid sequence (II):

EPKPVNQVYTVQISTKSGDWKSKC    (I), and

VFGKDLIYTLYYWKSSSSGKKT    (II).

18. The kit according to claim 15, wherein each monoclonal antibody is independently a complete antibody, an Fab' fragment or an F(ab')2 fragment.

19. The kit according to claim 15, wherein the first monoclonal antibody is a complete antibody, an Fab' fragment or an F(ab')2 fragment.

20. The kit according to claim 15, wherein the second monoclonal antibody is a complete antibody, an Fab' fragment or an F(ab')2 fragment.

21. The kit according to claim 15, wherein the buffer solution contains a concentration of 3 to 10 weight % of said at least one nonionic surfactant having an HLB value within a range of 12 to 30.

22. The kit according to claim 15, wherein the nonionic surfactant is polyethylene glycol mono-alkylphenol ether.

23. The kit according to claim 15, wherein the protein comprises skim milk.

24. The kit according to claim 15, wherein the insoluble solid carrier comprises beads.

* * * * *